United States Patent
Kimura et al.

(10) Patent No.: US 8,340,748 B2
(45) Date of Patent: Dec. 25, 2012

(54) FETUS ELECTROCARDIOGRAM SIGNAL MEASURING METHOD AND ITS DEVICE

(75) Inventors: Yoshitaka Kimura, Sendai (JP); Mitsuyuki Nakao, Sendai (JP); Takuya Ito, Sendai (JP); Kazunari Ohwada, Nishitokyo (JP)

(73) Assignee: Tohoku Techno Arch Co., Ltd., Sendai-shi (JP)

( * ) Notice: Subject to any disclaimer, the term of this patent is extended or adjusted under 35 U.S.C. 154(b) by 606 days.

(21) Appl. No.: 12/524,000

(22) PCT Filed: Jan. 22, 2008

(86) PCT No.: PCT/JP2008/050756
§ 371 (c)(1),
(2), (4) Date: Jul. 22, 2009

(87) PCT Pub. No.: WO2008/090862
PCT Pub. Date: Jul. 31, 2008

(65) Prior Publication Data
US 2010/0076330 A1    Mar. 25, 2010

(30) Foreign Application Priority Data

Jan. 23, 2007    (JP) .................................. 2007-012120

(51) Int. Cl.
*A61B 5/02*    (2006.01)
*A61B 5/04*    (2006.01)

(52) U.S. Cl. ........ 600/511; 600/506; 600/508; 600/509; 600/526

(58) Field of Classification Search .................. 600/506, 600/508–509, 511, 526
See application file for complete search history.

(56) References Cited

U.S. PATENT DOCUMENTS

| 6,751,498 B1 | 6/2004 | Greenberg et al. |
| 2005/0119583 A1 | 6/2005 | Fuller et al. |
| 2006/0189882 A1* | 8/2006 | Thomas ........................ 600/546 |

FOREIGN PATENT DOCUMENTS

| JP | 59 53009 | 4/1984 |
| JP | 2002 538872 | 11/2002 |
| JP | 2005 512719 | 5/2005 |
| WO | 2006 080167 | 8/2006 |

* cited by examiner

*Primary Examiner* — Nicole F Lavert
(74) *Attorney, Agent, or Firm* — Oblon, Spivak, McClelland, Maier & Neustadt, L.L.P.

(57) ABSTRACT

Disclosed are a fetus electrocardiogram signal measuring method and its device that are capable of measuring the electrocardiogram signals of a fetus even during fetus movements and even at a gestational age during which the measurement current is weak, without the need for reattaching the electrodes and providing any shield room, even if the mother is a hospitalized or ambulant pregnant woman. The fetus electrocardiogram signal measuring device includes (1) high input impedance electrodes, (2) region-variable ground electrodes, and (3) a differential amplifier circuit and an optimization computing section.

14 Claims, 8 Drawing Sheets

FETUS ELECTROCARDIOGRAM SIGNAL MEASURING METHOD AND ITS DEVICE

TECHNICAL FIELD

The present invention relates to a fetus electrocardiogram signal measuring method and its device for detecting electrocardiogram signals of a fetus, from a mother body in pregnancy.

BACKGROUND ART

Hitherto, in this type of the devices, fetus electrocardiogram signals by the scalp lead during the intrapartum period have been mainly used. This device is configured so that, a unipolar lead screw-type electrocardiogram electrode is passed through a birth canal via the opening of a vagina, to thereby be directly attached to a portion of a fetus, exposed to the outside of a uterus, for example, to the fetus head or buttock. Such a technique is disclosed in, for example, the Patent Document (1) by Rosen et al., or the Non-Patent Document (1) by Rosen, which are each described below.

These Patent Document (1) and Non-Patent Document (1) each set forth a measuring method for fetus electrocardiogram waveforms obtained from scalp electrodes. This method, however, is disadvantageous in that it limits the measurement time period to the intrapartum period, and that it increases the risk of causing infection to the fetus because this method is obviously an invasive one.

Likewise, regarding an intrauterine embedding type fetus monitoring device by Horio et al. set forth in the Patent Document (2) as described below, its method is also an invasive one in which a microcapsule is directly attached to a fetus through a uteroscope. Because this method requires an operation through a mother body for attaching the microcapsule to the fetus, it has, virtually, only limited application, and involves similar difficulties to those in the example of the above-described Patent Document (1).

Main methods that have hitherto been proposed for measuring a fetus electrocardiogram through the abdominal wall of a mother body, include a method based on a bipolar lead technique using a small number of electrode couples by Ogawa et al. set forth in the Non-Patent Document 2 as described below, and a method by Greenberg et al. set forth in the Patent Document (3) as described below, wherein a plurality of bipolar leads are combined so as to be mutually perpendicular to the direction of the body axis of a fetus.

These methods have been actively studied until recent years partly because there is the need to sandwich the central axis of a fetus between electrodes in order to reliably measure the fetus electrocardiogram, partly because it is possible to remove irregular noises that are mixed into the electrode couple commonly to their counterparts by taking the potential difference between the electrodes forming the counterparts, and partly because these methods are resistant to noise. However, the bipolar method is limited in data analysis technique. That is, this method requires two electrodes to obtain a single piece of measurement data, and the measurement of fetus electrocardiogram needs to cover the abdominal wall of a mother body with a large number of electrodes, making allowance for movements of a fetus in fetus activities. Moreover, when the fetus is small and hence the direction of the central axis of the fetus is hard to estimate, the measurement is difficult to perform. In particular, when fat components (vernix caseosa) of the fetus increases around the fetus as in the period at 26 to 36 weeks of gestation, and consequently the electric conductivity in the fetus electrocardiogram decreases, measured potentials come down to small values to thereby frequently make measurement impossible. Therefore, measurements by this bipolar method have often been performed in late pregnancy.

Peters M, Crowe J, Hayes-Gill B et al. in England, as shown in the Non-Patent document 3 described below, performed continuous measurements for long time period with five electrodes attached to the abdominal wall of a mother body, and analyzed fetus electrocardiogram signals that happened to be found therein, whereby they developed a device for measuring a fetus electrocardiogram, and attempted to productize it as a portable mother/fetus monitor. This method is an attempt to solve the problem that the measurement rate of the fetus electrocardiogram by the bipolar method is low. However, this method does not meet the condition that medical devices should satisfy. In other words, this method does not meet the performance requirement that the same result should be available whenever, wherever, and by whomever a measurement is performed. Therefore, it is not necessarily the case that this method can be used whenever an examination is needed, and sometimes, there occurs a need to wait one day or more before the result is available. This method, therefore, significantly restricts its availability, and does not provide a monitor usable whenever it is needed.

Furthermore, according to a method disclosed in the Non-Patent Document (4) described below, it is known that, in the bipolar electrode method, during a uterine contraction wherein a uterus contracts and the electromyogram increases, in the case where noise components abruptly change or the base line of signals irregularly increases/decreases during movements of a mother body, the S/N ratio decreases to thereby make the measurement impossible.

With this being the situation, as an alternative method to the bipolar electrode method, a unipolar method has now become mainstream wherein a plurality of measurement electrodes are attached to the abdominal wall of a mother body, and a reference electrode is placed at a position other than the measurement electrode positions on the mother body. The use of the unipolar method allows an increase in the number of electrodes on the abdominal wall, which increases occasions allowing measurements of fetus electrocardiogram signals. Such a technique is disclosed in, for example, the Patent Document 4 and the Non-Patent Document 5 each described below. However, as compared with bipolar electrode method, in the unipolar method, much noise is mixed into the circuit, and hence, in order to avoid it, shield lines are mainly used for use in reducing the noise. However, because the measurement must be performed in a shield room in many cases, this method is far from a device actually useful in monitoring on a clinical level. The unipolar method further involves the following problems: the electrode must be moved to find a position where and the electrode resistance is low and fetus electrocardiogram is satisfactorily measured; even if a measurement is being performed at an electrode position that has been found after the measurer's all efforts, there occurs the need to reattach the electrode when the fetus moves in fetus activities; and in cases wherein a mother as a subject is nervous, measurement is frequently impossible.

Therefore, monitoring for continuous long time including a time period of fetus movements in an ambulant or hospitalized pregnant woman is difficult. Moreover, even if the noise problem is factored out, in order to entirely cover the abdominal wall of the mother body, 100 to 200 electrodes are theoretically needed, which indicates that it is virtually impracticable to cover monitoring during fetus movements. However, as in the case of an exercise stress test performed in an adult electrocardiogram measurement, in a fetus also, an abnormality such as myocardial ischemia would be observed more frequently during fetus movements than at rest. Therefore, an electrode method usable during fetus movements as well as at its rest is desired. Moreover, since cases requiring urgent diagnoses often happen when the electrode method is used in clinical practice, a device usable for ambulant or hospitalized pregnant women, and adaptable to cases as many as possible, is desired.

However, there has hitherto been no implementation of low-noise and high-sensitivity fetus electrocardiogram signal measuring method and its device, as described above, capable of continuously measuring fetus electrocardiogram signals even during fetus movements, and usable for an ambulant or hospitalized pregnant woman without the need for reattaching the electrodes.

[Patent Document 1] PCT Japanese Translation Patent Publication No. 2002-532182
[Patent Document 2] Japanese Unexamined Patent Application Publication No. 2004-121733
[Patent Document 3] PCT Japanese Translation Patent Publication No. 2002-538872
[Patent Document 4] PCT Japanese Translation Patent Publication No. 2005-503883
[Non-patent document 1] Rosen KG: Fetus ECG waveform analysis in labour. Fetus monitoring. Physiology and techniques of antenatal and intrapartum assessment. Ad. Spencer JAD Castle House Publications. pp 184-187, 1989.
[Non-patent document 2] Ogawa Teruyuki: Time-series autoregressive analysis of normal fetus/neonate electrocardiogram R-R intervals. Actuality of time series II written and edited by Akaike Koji and Kitagawa Genshiro, 4th Chap. pp. 61-74, Asakura Shoten, 1995.
[Non-patent document 3] Peters M, et al: Monitoring the fetus heart non-invasively: a review of methods. J. Perinat. Med. 29(2001), pp. 408-416.
[Non-patent document 4] Zarzoso V and Nandi A K: Noninvasive fetus electrocardiogram extraction: Blind separation versus adaptive noise cancellation. IEEE Trans. Biomed. Eng. 48, 12-18, 2001.
[Non-patent document 5] Taylor M J O, et al.: Non-invasive fetus electrocardiography in singleton and multiple pregnancies. BJOG, 110, 668-78, 2003.
[Non-patent document 6] Yazaki Hiroyuki, Higuchi Masataka, Kyoso Masaki, Ishijima Masayuki: Unconscious sleep monitoring using large-area capacitor electrodes. The 46th Annual Meeting of Japan Soc, ME&BE, April, 2007, PS1-11-7.
[Non-patent document 7] Ishida Shuhei, Shiozawa Naruhiro, Fujiwara Yoshihisa, Makikawa Masaaki:
Electrocardiogram measurement during sleep with clothes worn using capacitively-coupled electrodes arranged at bedside. The 46th Annual Meeting of Japan Soc, ME&BE, April, 2007, PS1-11-8.

DISCLOSURE OF INVENTION

As described above, the conventional art has posed a problem that, in many cases, S/N ratios and the usability of the art become poor depending on conditions of a fetus or a mother body, so as to make measurement impossible, in such a way that the measurement place and the measurement range are limited, that the measurement is difficult during fetus movements or at a gestation age during which the measured potential is low, and that electrodes must be reattached when the position of a fetus has changed during fetus movements. In other words, these have been unsolvable problems because there have existed no technique for measuring non-stationary bioelectric potentials on the order of microvolts ($\mu V$).

In contrast, a new method for measuring the change in bioelectric current in a non-contact manner has appeared, as an unconstrained field measuring method. This method can freely set the shape of electrodes, and is becoming one of core techniques in the biological body measuring techniques in ubiquitous medical services, as wearable electrodes utilizing electrodes made of cloths etc. (Non-Patent Documents 6 and 7, and Patent Document 1).

This is an electricity measurement technique for measuring bioelectric potentials (voltage changes) by capacitive electrodes. According to this technique, because a bioelectric potential measurement is performed using capacitive coupling between electrodes and a biological body, non-contact bioelectric potential measurement is implementable. Furthermore, because capacitor-type coupling is formed between electrodes, measurement potential increases when there is an insulator around a measurement target, which would facilitate a fetus electrocardiogram measurement in about 30 weeks of gestation. The larger electrode allows better measurement. If a wide electrode is available, the measurement instability due to fetus movements in the above-described fetus electrocardiogram problems may be possibly eliminated. This is because, wherever a fetus may move to, the large electrodes can cover it, thus enabling measurement without the need to increase the number of electrodes for the fetus electrocardiogram.

Conversely, as defects accompanying the capacitor potential measurement, this electrode method involves the following problems: a local measurement is difficult; capacitive-coupled noise occurring between a measurement target and the periphery of a structure in a measurement place is prone to enter; if a ground electrode is made to be a capacitive electrode, the ground electrode also forms capacitive coupling with a measurement electrode and thus becomes no longer isolative, which infects a measured potential.

Furthermore, in the case of about 24 weeks in gestation wherein a direct current is considered to constitute main measurement current, this measurement method would actually make measurement difficult.

It is an object of the present invention to provide a convenient and extensively applicable method and its device for measuring fetus electrocardiogram signals, capable of measuring fetus electrocardiogram signals even during the fetus movements and even at a gestational age during which the measured potential is low, without the need for reattaching the electrodes and providing any special space such as a shield room, even if the mother is either a hospitalized or ambulant pregnant woman.

In order to achieve the above-described object, the present invention provides the following means:

[1] A fetus electrocardiogram signal measuring method for measuring, in an on-line manner, fetus electrocardiogram waveforms from a plurality of electrodes attached to the breast and the abdomen of a mother body during pregnancy, the method comprising the steps of: providing a high input impedance electrode section ($1a$) that directly acquires biological information, the high input impedance electrode section being composed of a plurality of measurement electrodes that constitute a high input impedance electrode in order to implement a high-accuracy electrode; providing a region-variable ground electrode section ($1b$) for addressing various positional variations of the fetus in order to implement a wide-area measurement, the region-variable ground electrode section being constituted of one or more region-variable ground electrodes (5a); providing a wide-area ground type high-sensitivity electrode including the high input impedance electrode section (1a), the region-variable ground electrode section (1b), and a differential amplification section (1c) serving as a main measuring member and having a differential characteristic; and providing an electrode optimization computing section (1d) that selects an optimal ground electrode region and an optimal electrode out of the combination of all of the electrodes, in order to optimally control the fetus position/state so that a maximum signal with low noise can be measured.

[2] The fetus electrocardiogram signal measuring method as recited in Item [1], wherein the high input impedance electrode section (1a) uses a shield cable comprising: a skin contact electrode section (2a) composed of a plurality of measurement electrodes (4) including a reference electrode (3); and a preamplification section (2b) having a characteristic of a high input impedance of 100 GΩ or above.

[3] The fetus electrocardiogram signal measuring method as recited in Item [2], wherein the skin contact electrode section (2a) constitutes a plurality of measurement electrodes (4) including the reference electrode (3), and each of the plurality of measurement electrodes is provided with a dielectric metal, an electrically-conductive polymeric gel, and connecting means therebetween.

[4] The fetus electrocardiogram signal measuring method as recited in Item [2], wherein the preamplification section (2b) is a preamplifier (2b-1) including an operational amplifier located between the differential amplification section (1c) and an electrode measurement point; and wherein the preamplification section (2b) can reduce the bias current flowing from the region-variable ground electrode section (1b) to the differential amplification section (1c) down to a current on the order of picoamperes, and can perform a potential difference measurement with a high sensitivity better than ±1 μV. However, it is desirable that the preamplification section (2b) is placed in the vicinity of the skin contact electrode section (2a).

[5] The fetus electrocardiogram signal measuring method as recited in Item [1], wherein the region-variable ground electrode section (1b) is a variable ground electrode capable of changing the measurement region of a biological signal in response to a change in the fetus position or in the fetus size depending on a gestational age, and to fetus movements; and wherein the region-variable ground electrode section (1b) comprises: region-variable ground electrodes (5a) each constituted of one or more plane electrodes; and an electrode optimal region constituting section (5b) constituting an optimal region on the basis of optimal region information output from the electrode optimization computing section (1d).

[6] The fetus electrocardiogram signal measuring method as recited in Item [5], wherein the region-variable ground electrodes (5a) are constituted of basic sheet ground electrodes each having one or more basic unit electrodes insulated from each other; and wherein the basic sheet ground electrode can be freely changed in size/shape. Here, the basic sheet ground electrodes are desirably high impedance electrodes such as cloth electrodes.

[7] The fetus electrocardiogram signal measuring method as recited in Item [5], wherein the electrode optimal region constituting section (5b) comprises: a threshold circuit (7a) that selects a combination of ground electrodes including fetus electrocardiogram components of a definite amount or above, out of the optimal region information input from the electrode optimization computing section (1d); and a relay circuit (7b) that implements the information obtained from the threshold circuit (7a) by a switch connection; and wherein, on the basis of the optimal region information output from the electrode optimization computing section (1d), the size/shape of each of the ground electrodes is changed by freely combining a plurality of the basic sheet ground electrodes adhered to a biological body and connecting them to each other by the relay circuit (7b), to thereby realize optimal ground electrodes matched with fetus movements/fetus positional variations.

[8] The fetus electrocardiogram signal measuring method as recited in Item [1], wherein the differential amplification section (1c) comprises: the high input impedance electrode section (1a); a differential amplifier (8a) for amplifying and differentiating a signal from the input of the region-variable ground electrode; a multiplexer (8b) that converts multiple inputs into a single input; and an A/D converter (8c); wherein the potential of each measurement channel output from a signal output section is obtained by subtracting the difference between the potential of the reference electrode and the ground potential from the difference between the potential of each channel and the ground potential; and wherein, by placing the reference electrode and the region-variable ground electrode at the same region, the voltage difference between in-phase voltage signals of the reference electrode and region-variable ground electrode is made to be zero, and the potential of each measurement channel is made to be the difference between the potential of each channel and the potential of the region-variable ground electrode.

[9] The fetus electrocardiogram signal measuring method as recited in Item [1], wherein the electrode optimization computing section (1d) comprises: a fetus electrocardiogram signal recognition section (9a) that recognizes a fetus electrocardiogram signal; a ground electrode recognition section (9c) that, on the basis of each channel information from the fetus electrocardiogram signal recognition section (9a), recognizes a basic unit ground electrode (indifferent ground electrode) including no fetus electrocardiogram signal in every measurement channel, and a variable ground electrode (optimal variable ground electrode) including fetus electrocardiogram signals to a maximum degree in any measurement channel; a measurement electrode recognition section (9b) that recognizes a measurement electrode (indifferent measurement electrode) by which no fetus electrocardiogram signal is measured when the optimal variable ground electrode is used; and a basic computing section (9d) capable of cancelling noise that is electrode noise other than ground electrode-derived noise and that is common to all the measurement electrodes, by taking the difference in potential between each of the measuring electrodes and the indifferent electrode.

Here, information on the optimal variable ground electrode and the indifferent ground electrode is output to the electrode optimal region constituting section (5b) in the region-variable ground electrode section (1b), as optimal region information, along with each channel information from the fetus electrocardiogram signal recognition section (9a).

Moreover, in the measurement electrode recognition section (9b), it is desirable that the fetus electrocardiogram signal is automatically recognized by autocorrelation.

However, if there exists no basic unit ground electrode including no fetus electrocardiogram signal in any measurement channel, the indifferent ground electrode is regarded as a minimum ground potential electrode including a minimum fetus cardiac potential in each measurement channel, or as zero. Likewise, regarding the indifferent measurement electrode, it is regarded as a minimum fetus cardiac potential measurement electrode, or as zero.

[10] A fetus electrocardiogram signal measuring device for measuring, in an on-line manner, fetus electrocardiogram waveforms from a plurality of electrodes attached to the breast and the abdomen of a mother body during pregnancy, the device comprising: a high input impedance electrode section (1a) that directly acquires biological information, the high input impedance electrode section being composed of a plurality of measurement electrodes that constitute a high input impedance electrode in order to implement a high-accuracy electrode; a region-variable ground electrode section (1b) for addressing various positional variations of the fetus in order to implement a wide-area measurement, the region-variable ground electrode section being constituted of one or more region-variable ground electrodes (5a); a wide-area ground type high-sensitivity electrode including the high input impedance electrode section (1a), the region-variable ground electrode section (1b), and a differential amplification section (1c) serving as a main measuring member and having a differential characteristic; and an electrode optimization computing section (1d) that selects an optimal ground electrode region and an optimal electrode out of the combinations of all of the electrodes, in order to optimally control the fetus position/state so that a maximum signal with low noise can be measured.

[11] The fetus electrocardiogram signal measuring device as recited in Item [10], wherein the high input impedance electrode section (1a) comprises: a skin contact electrode section (2a) composed of a plurality of measurement electrodes (4) including a reference electrode (3), and a cable; a preamplification section (2b) having a characteristic of a high input impedance of 100 GΩ or above; and a shield cable.

[12] The fetus electrocardiogram signal measuring device as recited in Item [11], wherein the skin contact electrode section (2a) constitutes a plurality of measurement electrodes (4) including the reference electrode (3), and each of the plurality of measurement electrodes is provided with a dielectric metal, an electrically-conductive polymeric gel, and connecting means therebetween.

[13] The fetus electrocardiogram signal measuring device as recited in Item [11], wherein the preamplification section (2b) is a preamplifier (2b-1) including an operational amplifier located between the differential amplification section (1c) and an electrode measurement point; and wherein the preamplification section (2b) is configured to be capable of: reducing the bias current flowing from the region-variable ground electrode section (1b) to the differential amplification section (1c) down to a current on the order of picoamperes; and performing a potential difference measurement with a high sensitivity better than ±1 μV. However, it is desirable that the preamplification section (2b) is placed in the vicinity of the skin contact electrode section (2a).

[14] The fetus electrocardiogram signal measuring device as recited in Item [10], wherein the region-variable ground electrode section (1b) is a variable ground electrode capable of changing the measurement region of a biological signal in response to a change in the fetus position or in the fetus size depending on a gestational age, and to fetus movements; and wherein the region-variable ground electrode section (1b) comprises: region-variable ground electrodes (5a) each constituted of one or more plane electrodes; and an electrode optimal region constituting section (5b) constituting an optimal region on the basis of optimal region information output from the electrode optimization computing section (1d).

[15] The fetus electrocardiogram signal measuring device as recited in Item [14], wherein the region-variable ground electrodes (5a) are constituted of basic sheet ground electrodes each having width of one or more basic unit electrodes insulated from each other; and wherein the basic sheet ground electrode can be freely changed in size/shape.

[16] The fetus electrocardiogram signal measuring device as recited in Item [14], wherein the electrode optimal region constituting section (5b) comprises: a threshold circuit (7a) that selects a combination of ground electrodes including fetus electrocardiogram components of a definite amount or above, out of the optimal region information input from the electrode optimization computing section (1d); and a relay circuit (7b) that implements the information obtained from the threshold circuit (7a) by a switch connection; and wherein, on the basis of the optimal region information output from the electrode optimization computing section (1d), the size/shape of each of the ground electrodes is changed by freely combining a plurality of the basic sheet ground electrodes adhered to a biological body and connecting them to each other by the relay circuit (7b), to thereby realize optimal ground electrodes matched with fetus movements/fetus positional variations.

[17] The fetus electrocardiogram signal measuring device as recited in Item [10], wherein the differential amplification section (1c) comprises: the high input impedance electrode section (1a); a differential amplifier (8a) for amplifying and differentiating a signal from the input of the region-variable ground electrode; a multiplexer (8b) that converts multiple inputs into a single input; and an A/D converter (8c); wherein the potential of each measurement channel output from a signal output section is obtained by subtracting the difference between the potential of the reference electrode and the ground potential from the difference between the potential of each channel and the ground potential; and wherein, by placing the reference electrode and the region-variable ground electrode at the same region, the voltage difference between in-phase voltage signals of the reference electrode and region-variable ground electrode is made to be zero, and the potential of each measurement channel is made to be the difference between the potential of each channel and the potential of the region-variable ground electrode.

[18] The fetus electrocardiogram signal measuring device as recited in Item [10], wherein the electrode optimization computing section (1d) comprises: a fetus electrocardiogram signal recognition section (9a) that recognizes a fetus electrocardiogram signal; a ground electrode recognition section (9c) that, on the basis of each channel information from the fetus electrocardiogram signal recognition section (9a), recognizes a basic unit ground electrode (indifferent ground electrode) including no fetus electrocardiogram signal in every measurement channel, and a variable ground electrode (optimal variable ground electrode) including fetus electrocardiogram signals to a maximum degree in any measurement channel; a measurement electrode recognition section (9b) that recognizes a measurement electrode (indifferent measurement electrode) by which no fetus electrocardiogram signal is measured when the optimal variable ground electrode is used; and a basic computing section (9d) capable of cancelling noise that is electrode noise other than ground electrode-derived noise and that is common to all the measurement electrodes, by taking the difference in potential between each of the measuring electrodes and the indifferent electrode.

Here, information on the optimal variable ground electrode and the indifferent ground electrode is output to the electrode optimal region constituting section (5b) in the region-variable ground electrode section (1b), as optimal region information, along with each channel information from the fetus electrocardiogram signal recognition section (9a).

Moreover, in the measurement electrode recognition section (9b), it is desirable that the fetus electrocardiogram signal is automatically recognized by autocorrelation.

However, if there exists no basic unit ground electrode including no fetus electrocardiogram signal in any measurement channel, the indifferent ground electrode is regarded as a minimum potential ground electrode including a minimum fetus cardiac potential in each measurement channel, or as zero. Likewise, regarding the indifferent measurement electrode, it is regarded as a minimum fetus cardiac potential measurement electrode, or as zero.

In summary, the present invention includes: (1) introducing high input impedance electrodes for low-noise and high-accuracy measurement, the high input impedance electrodes being resistant to mixture of noise and independent of skin resistance, and ensuring high accuracy, (2) introducing a wide-area ground electrode (region-variable ground electrode) allowing wide-area measurements with high-accuracy just as it is, in order to realize measurements independent of fetus movements and fetus positional changes, and (3) a differential amplifier circuit and an optimization computing section allowing measurement of minute bioelectric potential on the order of microvolts ($\mu V$) by appropriately connecting the above-described electrodes by electronic circuits.

BEST MODE FOR CARRYING OUT THE INVENTION

Hereinafter, embodiments according to the present invention will be described with reference to the drawings.

Figure 1:
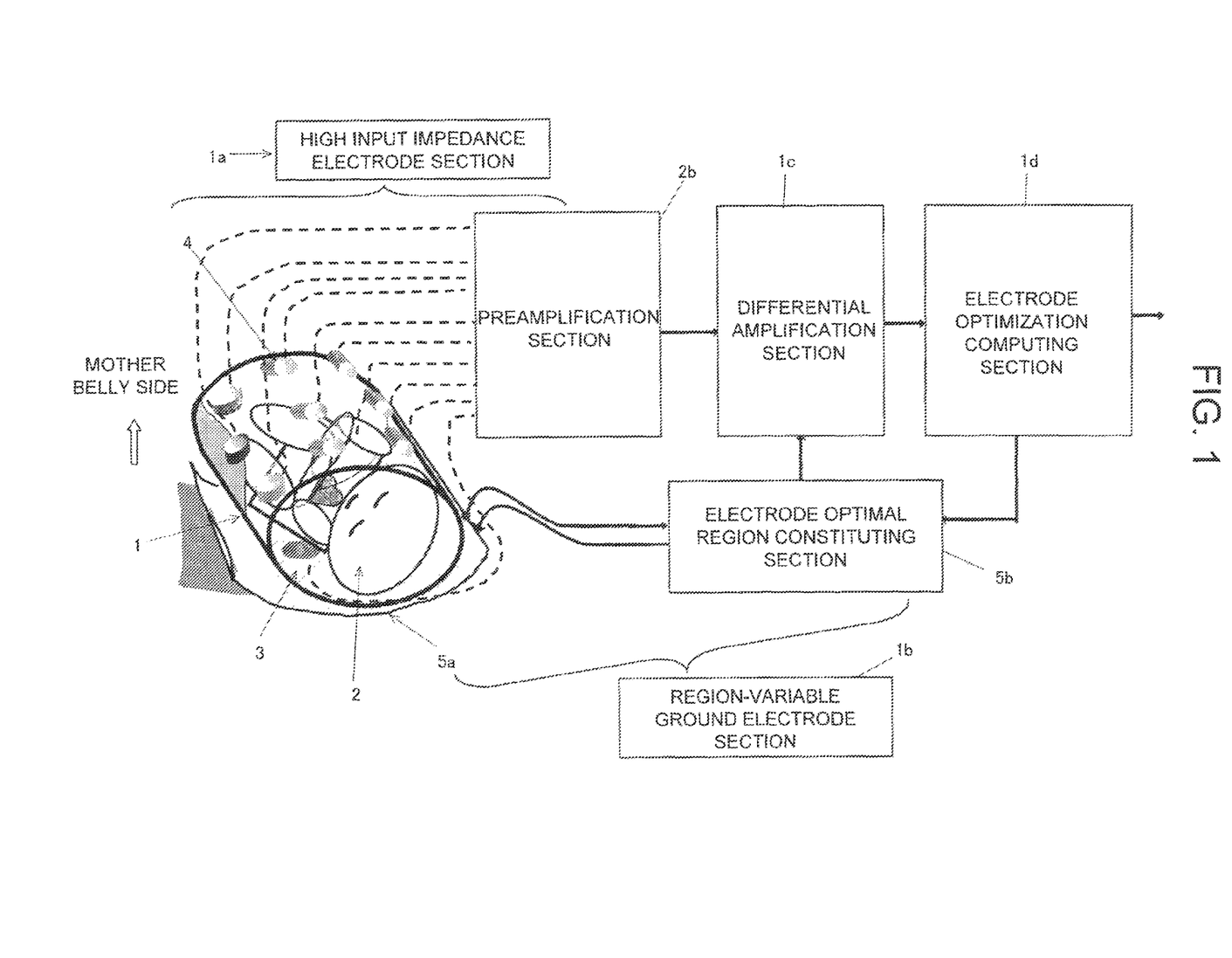
FIG. 1 is a diagram showing a schematic configuration of a fetus electrocardiogram signal measuring device according to an embodiment of the present invention.

FIG. 1 is a diagram showing a schematic configuration of a fetus electrocardiogram signal measuring device according to an embodiment of the present invention.

In FIG. 1, reference numeral 1 denotes a mother body, 2 denotes a fetus inside the mother body 1, 3 denotes a reference electrode, and 4 denotes measurement electrodes. Furthermore, reference numeral 1a denotes a high input impedance electrode section. The high input impedance electrode section 1a equivalently amplifies an input potential from the measurement electrodes 4 and the reference electrode 3 by a preamplification section 2b including a preamplifier, and converts the input potential into a high input impedance biometric potential signal.

The reference electrode 3 is attached to the back of the mother body along with a region-variable ground electrode (basic sheet ground electrode) 5a. Moreover, a plurality of measurement electrodes 4 are attached to the abdominal wall of the mother body. Here, the region-variable ground electrode 5a is constituted of basic sheet ground electrode having one or more basic unit electrodes insulated from each other, wherein the size/shape of the basic sheet ground electrode is freely changeable.

Reference numeral 1b denotes a region-variable ground electrode section composed of the region-variable ground electrode 5a and an electrode optimal region constituting section 5b. In the region-variable ground electrode section 1b, the region-variable ground electrode 5a constituted of one or more plane electrodes is connected to the electrode optimal region constituting section 5b so that maximum fetus electrocardiogram signals can be obtained in the electrode optimal region constituting section 5b, and the obtained signals are input as ground electrode potentials of a differential amplifier in a differential amplification section 1c. The differential amplification section, denoted by reference numeral 1c, performs differential amplification and A/D conversion with respect to measured signals. Reference numeral 1d denotes an electrode optimization computing section. The electrode optimization computing section 1d, for example, recognizes fetus electrocardiogram signals in each measured signal by making use of autocorrelation, and outputs the correlation to the region-variable ground electrode section 1b for each channel. It also outputs, as final measured signals, differences between a channel potential with minimum correlation and other channel potentials.

Figure 2:
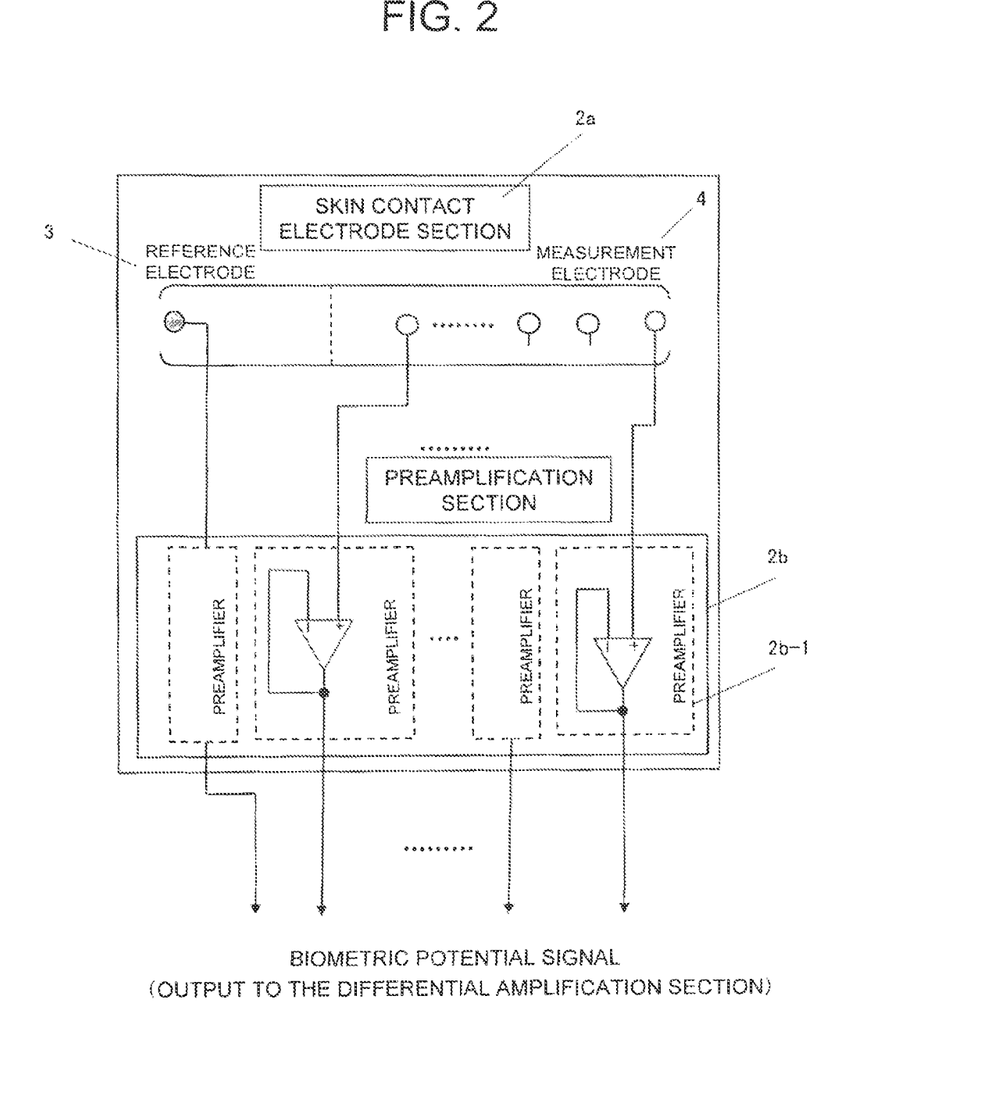
FIG. 2 is a block diagram of a high input impedance electrode section according to the present invention.

Next, the high input impedance electrode section 1a will be described with reference to FIG. 2.

The high input impedance electrode section 1a includes the measurement electrodes 4 and the reference electrode 3 constituting a skin contact electrode section 2a, wherein the measurement electrodes 4 and the reference electrode 3 are the same type of high input impedance point electrodes. By forming the measurement electrodes 4 and the reference electrode 3 as the same type of point electrodes in this way, the in-phase signal rejection ratio in the differential amplification section 1c does not increase. Furthermore, by providing the preamplification section 2b having the preamplifiers 2b-1, high input impedance of 100 GΩ or above can be implemented.

The skin contact electrode section 2a is composed of a plurality of measurement electrodes including the reference electrode 3, and each of the measurement electrodes 4 employs a dielectric metal, an electrically-conductive polymeric gel (wet gel), and a cable.

The preamplification section 2b is composed of preamplifiers 2b-1 including operational amplifiers located between the differential amplification section 1c and an electrode measurement points. The preamplification section 2b can reduce the bias current flowing from the region-variable ground electrode section 1b to the differential amplification section 1c down to a current on the order of picoamperes, and can perform a potential difference measurement with a high sensitivity better than ±1 µV.

In the present invention, in order to solve the problems associated with the conventional art, there will be described below the principle of a semi-capacitive electrode method (wide-area ground type high-sensitivity electrode method) wherein a capacitive coupling type potential measurement is performed by combining an ordinary metallic circuit and a capacitive electrode; a setting method for circuit conditions by the voltage follower analysis based on an equivalent circuit; and measured results by an actual electric circuit for implementing the above-described setting method. Thereby, a high-accuracy body surface potential field measurement with accuracy of ±1 µV that has been impossible until now, can be implemented.

In the present invention, a simulation circuit for bioelectric potential measurement using a capacitive electrode was constructed, and a relational expression between the target potential to be measured and the measured potential when the capacitive electrode is used as a ground electrode was created. Thereby, it was examined how the ground electrode potential participates in the measured signal, and also it was derived a condition under which the biological wide-area ground type high-sensitivity electrode method as a bioelectric potential measuring method using a wide-area ground electrode holds.

Figure 3:
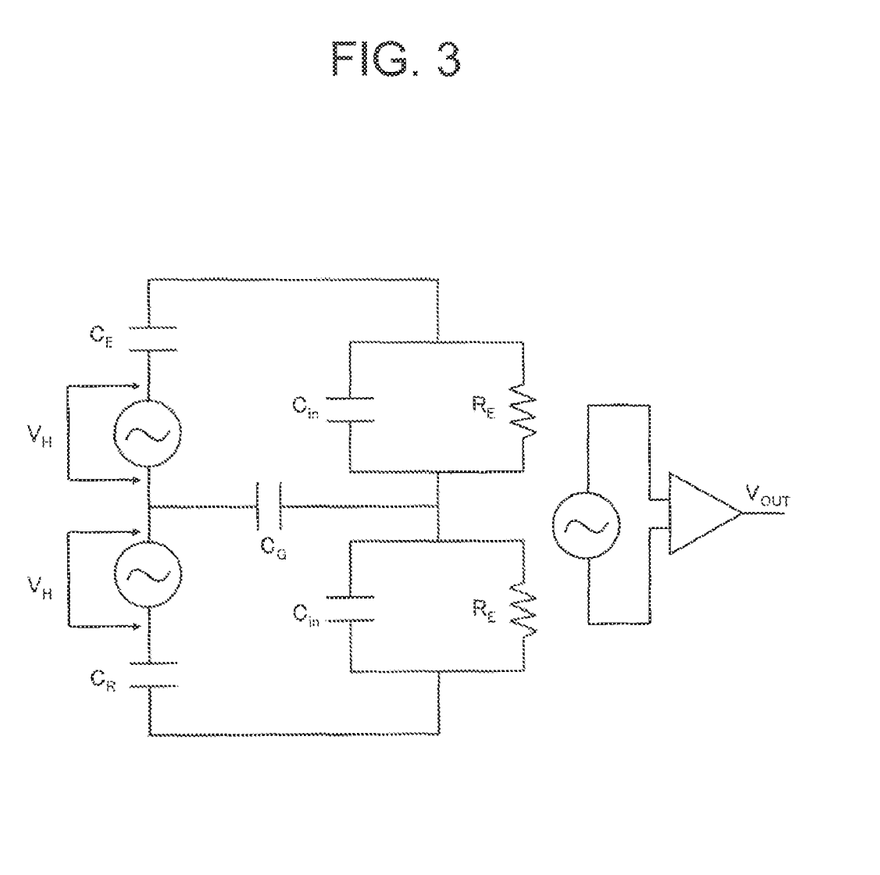
FIG. 3 is a diagram showing a bioelectric potential measurement simulation by a ground capacitive electrode according to the present invention.

FIG. 3 is a diagram showing a bioelectric potential measurement simulation by a ground capacitive electrode according to the present invention.

In FIG. 3 and the following expression (1), let A be an amplification factor, $C_E$ be a capacitive coupling potential of a measurement electrode, $R_E$ be a measurement electrode resistance, $C_{in}$ be an equivalent capacitance potential of a preamplifier circuit, and $C_G$ be a capacitive coupling potential of the ground electrode. Furthermore, let $V_H$ be a fetus cardiac potential, $V_{out}$ be a measured potential, and $C_R$ be a reference electrode potential.

$$V_{out} = AC_G\{[C_E/[C_{in}(C_E+C_G)+C_E C_G]] - [C_R/[C_{in}(C_R+C_G)+C_R C_G]]\}V_H \quad (1)$$

The above expression (1) shows a relationship between the fetus cardiac potential and the measured potential that are derived from the simulation. Here, the ground electrode capacitance $C_G$ appears positive in the measured potential $V_{out}$. If the same kind of electrodes are used for the measurement electrodes and the reference electrode, the denominators within brackets [ ] in the above expression (1) can be assumed to be equal to each other. It can also been seen that, when the capacitive coupling potential $C_G$ of the ground electrode is sufficiently higher than the capacitive coupling potential $C_E$ of the measurement electrode, the reference electrode potential $C_R$, and the equivalent capacitance potential $C_{in}$ of the preamplifier circuit, the capacitive coupling potential $C_G$ of the ground electrode directly participates in the measured potential.

The present invention is unprecedented to date which treats the ground electrode in the same way as the measurement electrode by using the capacitive coupling, and which enlarges the measurement range while realizing a high sensitivity.

Next, the region-variable ground electrode section 1b will be described in detail with reference to FIG. 4.

Figure 4:
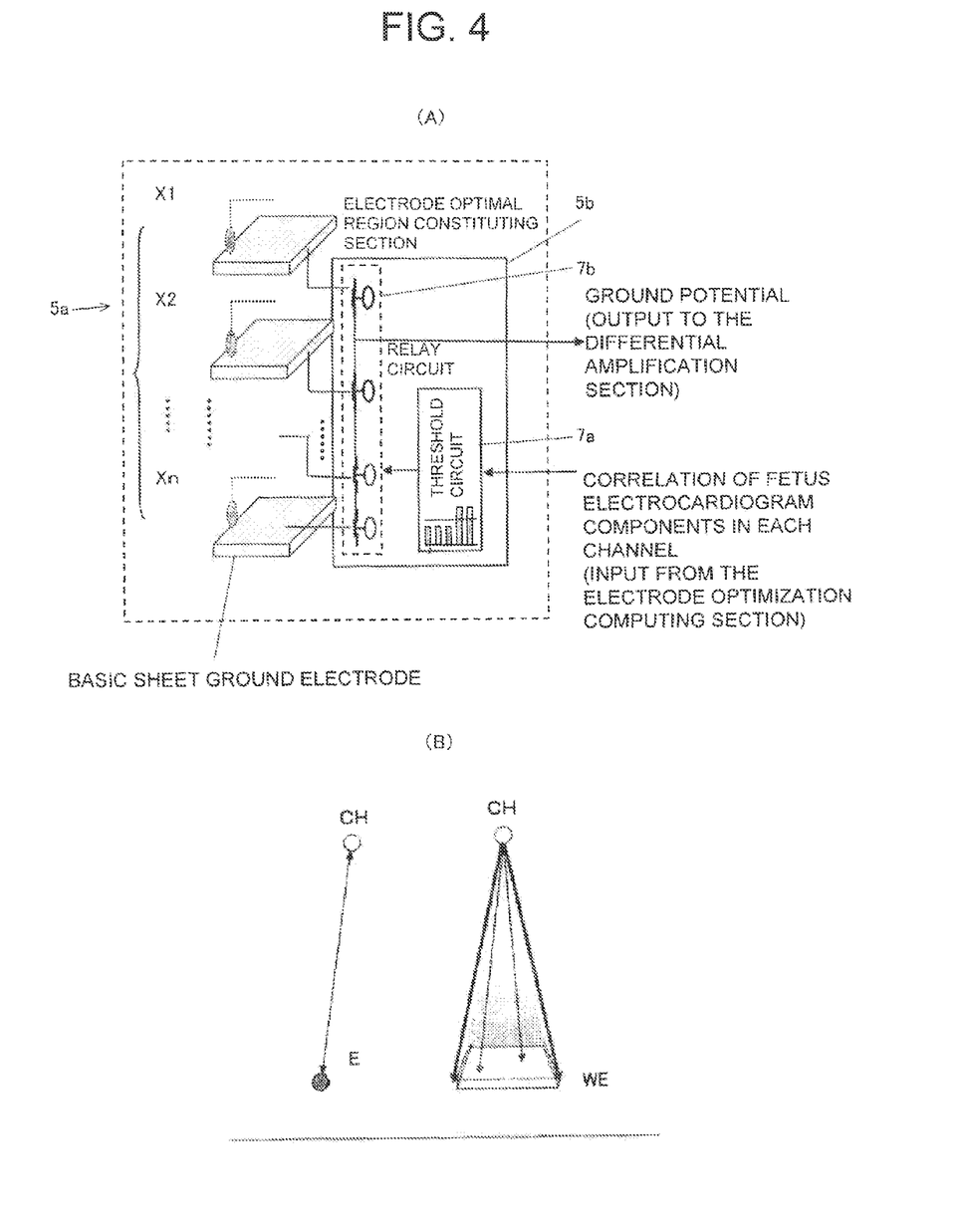
FIG. 4 shows a block diagram of a region-variable ground electrode section according to the present invention, and an explanatory diagram of a plane electrode.

FIG. 4(A) shows the configuration of the region-variable ground electrode section 1b. The region-variable ground electrode section 1b is composed of the region-variable ground electrode 5a to be attached to the back of a mother body and the electrode optimal region constituting section 5b.

The region-variable ground electrode 5a is composed of one or more basic sheet ground electrodes X1 . . . Xn, and the reference electrode 3 is located in the vicinity of the region-variable ground electrode 5a. The basic sheet ground electrodes X1 . . . Xn are each an electrically-conductive plane electrode, and their surface electric resistance is preferably 0.1Ω or below. The size of each of the basic sheet ground electrodes X1 . . . Xn may be freely set. The electrode optimal region constituting section 5b is configured to freely connect the basic sheet ground electrodes X1 . . . Xn to each other by a relay circuit 7b so that fetus electrocardiogram signals can be measured optimally in response to fetus movements. The optimal combination at this time comprises optimal region information obtained from the electrode optimization computing section 1d shown in FIG. 1 and a threshold circuit 7a.

FIG. 4(B) is a diagram showing a comparison between the conventional method and the method according to the present invention. The left-side figure in FIG. 4(B) shows the conventional method. Here, CH represents a measurement electrode, and E represents a point electrode. On the other hand, the right-side figure in FIG. 4(B) shows the method according to the present invention, wherein WE represents a plane electrode. In the measurement by the point electrode E according to the conventional method, merely potential changes on the straight line (CH-E) connecting the measurement electrode CH and the point electrode E is measured. In contrast, in the present invention, as shown in the right-side figure, since WE is a plane electrode, a wide-ranged measurement is possible. That is, in this method, the sum total potentials of all points on the point electrode CH and plane electrode WE in any shape can be measured. However, in a method wherein the point electrode is simply replaced with the plane electrode in order to realize the purpose described above, a bioelectric potential signal on the order of microvolts cannot be measured. This is because, as problems associated with the plane electrode, there are a problem concerning polarization potential noise occurring between the electrode surface and human skin and a problem concerning noise due to degradation of in-phase rejection ratio owing to variations in adhesion between the skin and the electrode. With the plane electrode enlarged, the polarization potential noise becomes 100 µV or above by itself, which makes impossible the measurement of a bioelectric potential signal on the order of microvolts. In the present invention, the polarization potential noise was cancelled by using the high input impedance electrodes for the measurement electrodes 4 to reduce the bias current between the electrodes. Furthermore, the degradation of the in-phase rejection ratio occurring in the differential amplification section 1c was cancelled by changing only the region-variable ground electrodes 5a into plane electrodes with the measurement electrodes 4 and the reference electrode 3 remaining as the point electrodes. The basic sheet ground electrodes X1 . .

. Xn are effective even if they are each constituted by one or more sheets of cloth electrodes. In this case, capacitive coupling is formed between the electrode cloths and the skin, and therefore, a high input impedance is realized even on the ground electrode side, thereby allowing reduction in noise.

Next, the differential amplification section $1c$ will be explained in detail with reference to FIG. 5.

Figure 5:
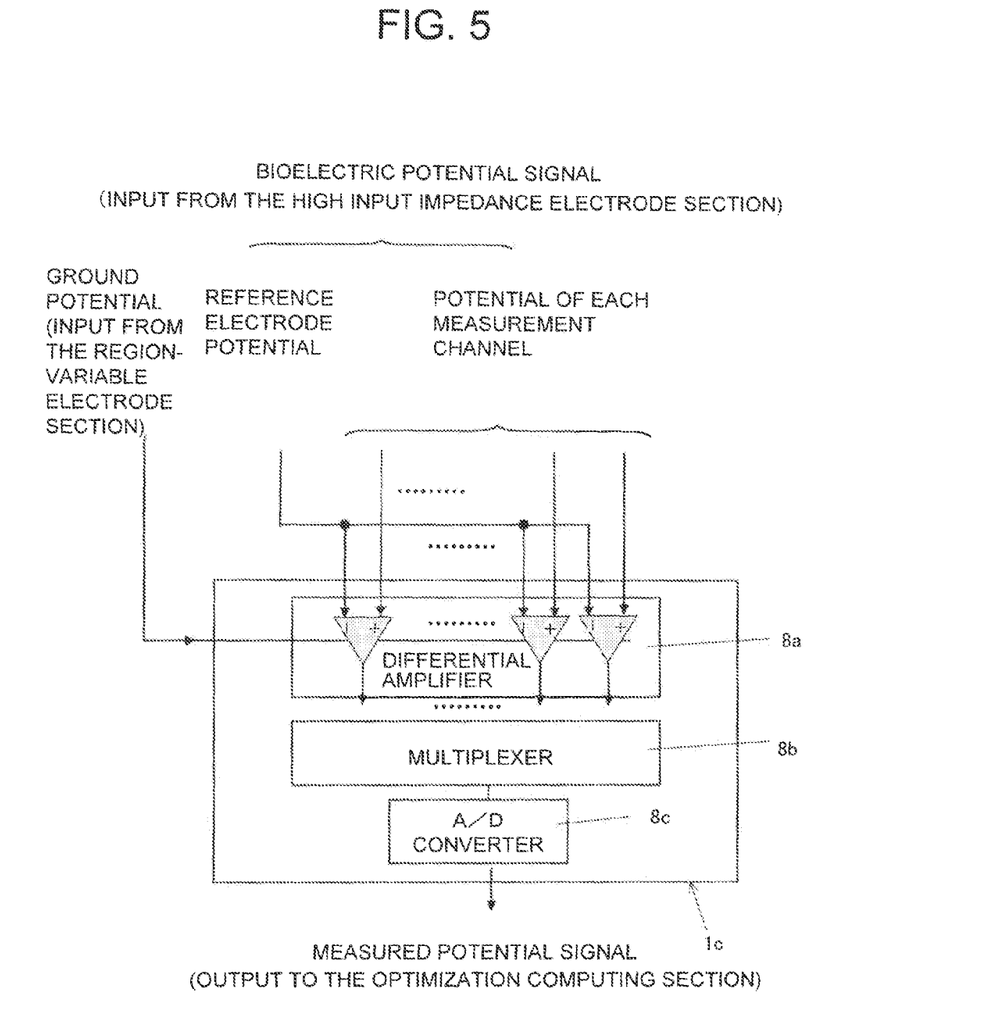
FIG. 5 is a block diagram of a differential amplifier according to the present invention.

In FIG. 5, the differential amplification section $1c$ includes a differential amplifier $8a$, a multiplexer $8b$ for high speed on-line processing, and an A/D converter $8c$. The potential of each measurement channel output from a signal output section is obtained by subtracting the difference between the reference electrode potential and the ground potential from the difference between the potential of each channel and the ground potential. Therefore, by placing the reference electrode 3 and the region-variable ground electrode $5a$ at the same region, the voltage difference between in-phase voltage signals of the reference electrode 3 and region-variable ground electrode $5a$ can be made to be zero. As a result, the potential of each measurement channel can be made to be the difference between the potential of each channel and the region-variable ground electrode potential.

Now, the electrode optimization computing section $1d$ will be described in detail with reference to FIG. 6.

Figure 6:
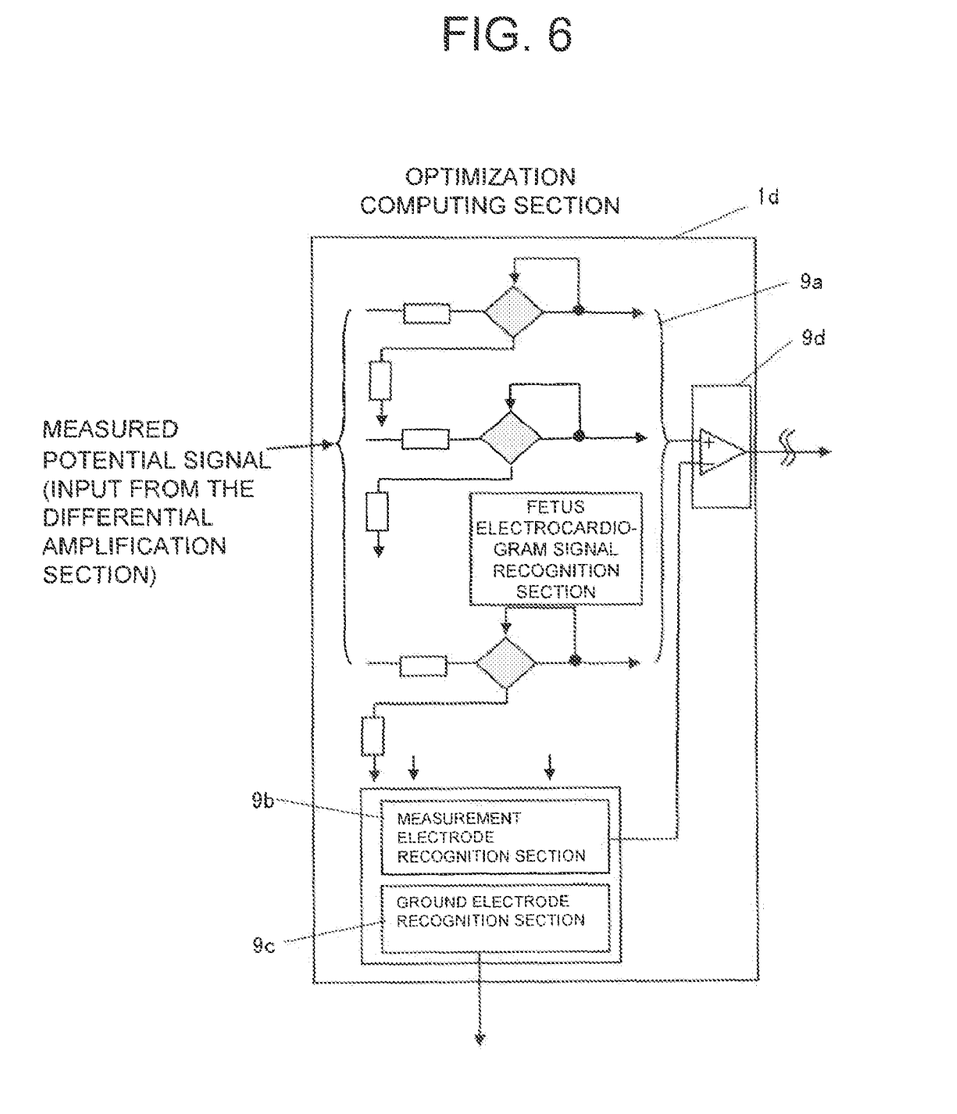
FIG. 6 is a block diagram of an electrode optimization computing unit according to the present invention, wherein an example of automatic electrode control algorism during fetus movements is illustrated.

In FIG. 6, the electrode optimization computing section $1d$ is a computing section for implementing an optimal measurement for the measurement of fetus electrocardiogram signals on the basis of measured potential signals in each channel. The electrode optimization computing section $1d$ includes a fetus electrocardiogram signal recognition section $9a$, a measurement electrode recognition section $9b$, a ground electrode recognition section $9c$, and a basic computing section $9d$.

In the present invention, regarding the size and/or the shape of the ground electrode, it is possible to determine their maximum measurement state by manipulating only connection states between a plurality of the basic sheet ground electrodes without the need of changing positions or characteristics of the measurement electrodes. Moreover, as described above, main problems occurring when the plane electrodes are used can be avoided. Furthermore, when fetus electrocardiogram signals cannot be obtained due to fetus movements, the connection allowing measurement can be immediately restored only by connecting more basic sheet ground electrodes.

In the fetus electrocardiogram signal recognition section $9a$, fetus electrocardiogram signals in each channel are quantifies and recognized by, for example, autocorrelation of the fetus electrocardiogram cycle. The information on the recognized fetus electrocardiogram signals, for example, the autocorrelation amount enters from the ground electrode recognition section $9c$ into the electrode optimal region constituting section $5b$ in the region-variable ground electrode section $1b$, thereby implementing an optimal ground electrode.

Furthermore, from e.g., the autocorrelation amount that has been entered into the measurement electrode recognition section $9b$, the indifferent measurement electrode is estimated, and thus in-phase potential noise in each measured potential are eliminated by the basic computing section $9d$.

Here, in the electrode optimization computing section $1d$ and the electrode optimal region constituting section $5b$, the optimal control means a measurement optimization by the maximization of a fetus cardiac potential component in a state wherein fetus electrocardiogram signals are weak during fetus movements or at about 30 weeks of gestation, whereas no optimal control may be required at rest at about 24 weeks or about 40 weeks of gestation, wherein fetus electrocardiogram signals can be stably measured with doing nothing. In the latter case, these optimization mechanisms need not be used.

Figure 7:
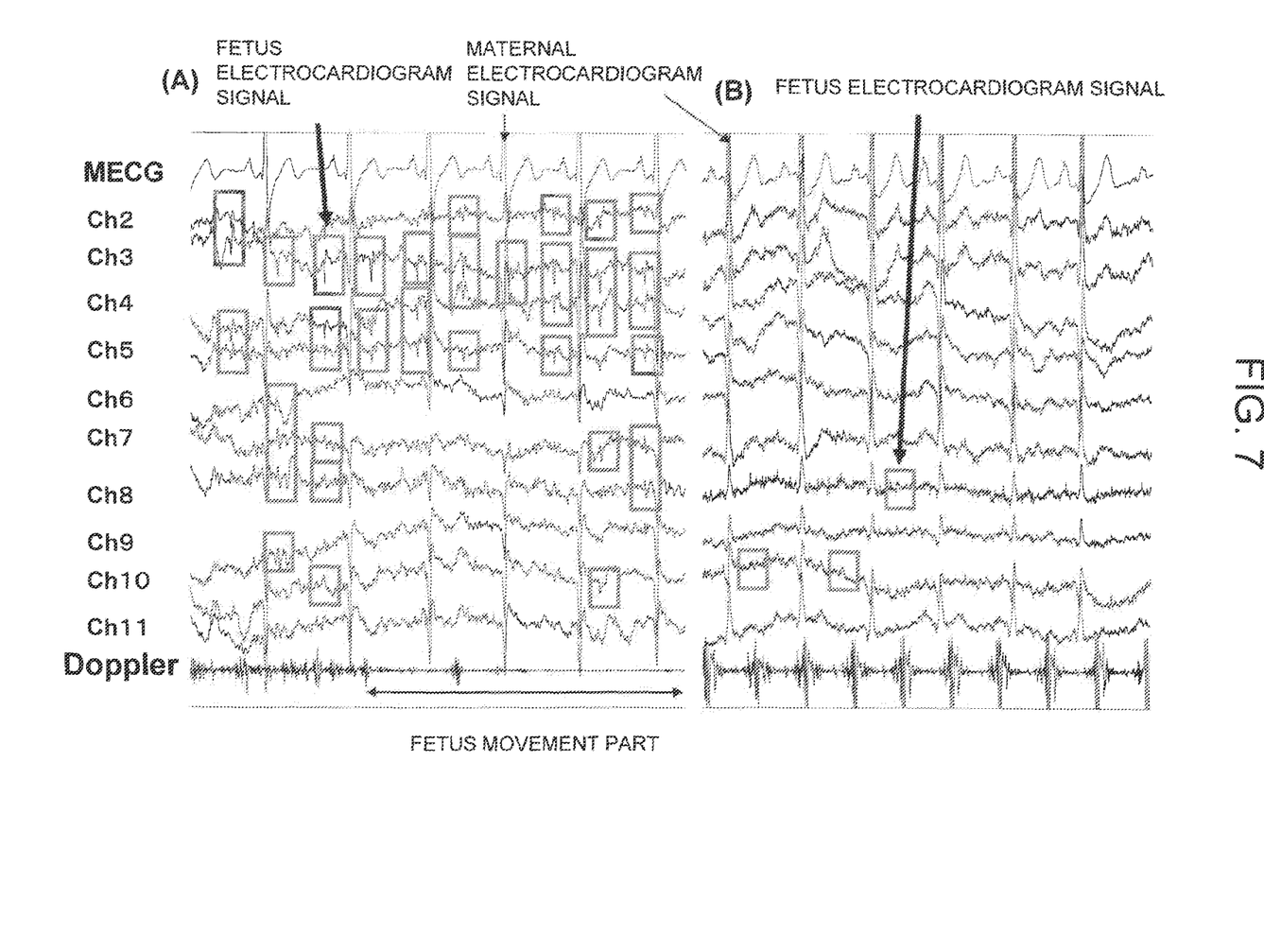
FIG. 7 shows diagrams illustrating measurement examples of fetus electrocardiogram signals according to the present invention at the time when the electrocardiogram signals are weak at 33 weeks of gestation.

FIG. 7 shows measurement examples of weak electrocardiogram signals at 33 weeks of gestation.

In these examples, an electrode of silver-silver chloride, which is dielectric metal, was used as a measurement electrode, and wet gel was used as electrically-conductive polymeric gel. The basic sheet ground electrodes were each formed by combining six sheets of plane electrodes each having a size of 2.5 cm×4 cm. The way of connecting these basic sheet ground electrodes was selected being matched with fetus movements to measure fetus electrocardiogram signals. By using cloth electrodes made of copper-nickel plated taffeta as the electrode cloths, fetus electrocardiogram component could be measured. FIG. 7(B) shows the measured result of fetus electrocardiogram signals measured in a shield room by the same method (conventional method) as that by Tailor et al. Because of weak potentials, no fetus electrocardiogram signal has been measured by the conventional method. In contrast, by the method according to the present invention as shown in FIG. 7A, fetus electrocardiogram signals have been consecutively and distinctly measured as shown in small frames in the figure. Here, "Doppler" in the figure represents fetus heart Doppler signals. The shape change of the fetus heart Doppler signal represents positional changes of the fetus heart with respect to a Doppler probe, namely, fetus movements. In the method according to the present invention, it can be seen that the fetus electrocardiogram signals have been consecutively obtained in spite of the fact that the fetus heart Doppler signals have become unmeasurable because the fetus heart Doppler signals have come off due to the fetus movements. In contrast, in the conventional method shown in FIG. 7(B), even at rest during which the fetus heart Doppler signals should be consecutively obtained, measured fetus electrocardiogram signals have been small in number, and in some instances, no fetus electrocardiogram signal have been measurable.

That is, in contrast to the conventional method wherein the measurement of fetus electrocardiogram signals is very difficult when the fetus component is small, the method according to the present invention allows the fetus electrocardiogram signals (within the small frames) to be consecutively measured in a stable manner even if the "Doppler" signals cannot be measured due to fetus movements. Here, "MECG" denotes a maternal electrocardiogram.

Figure 8:
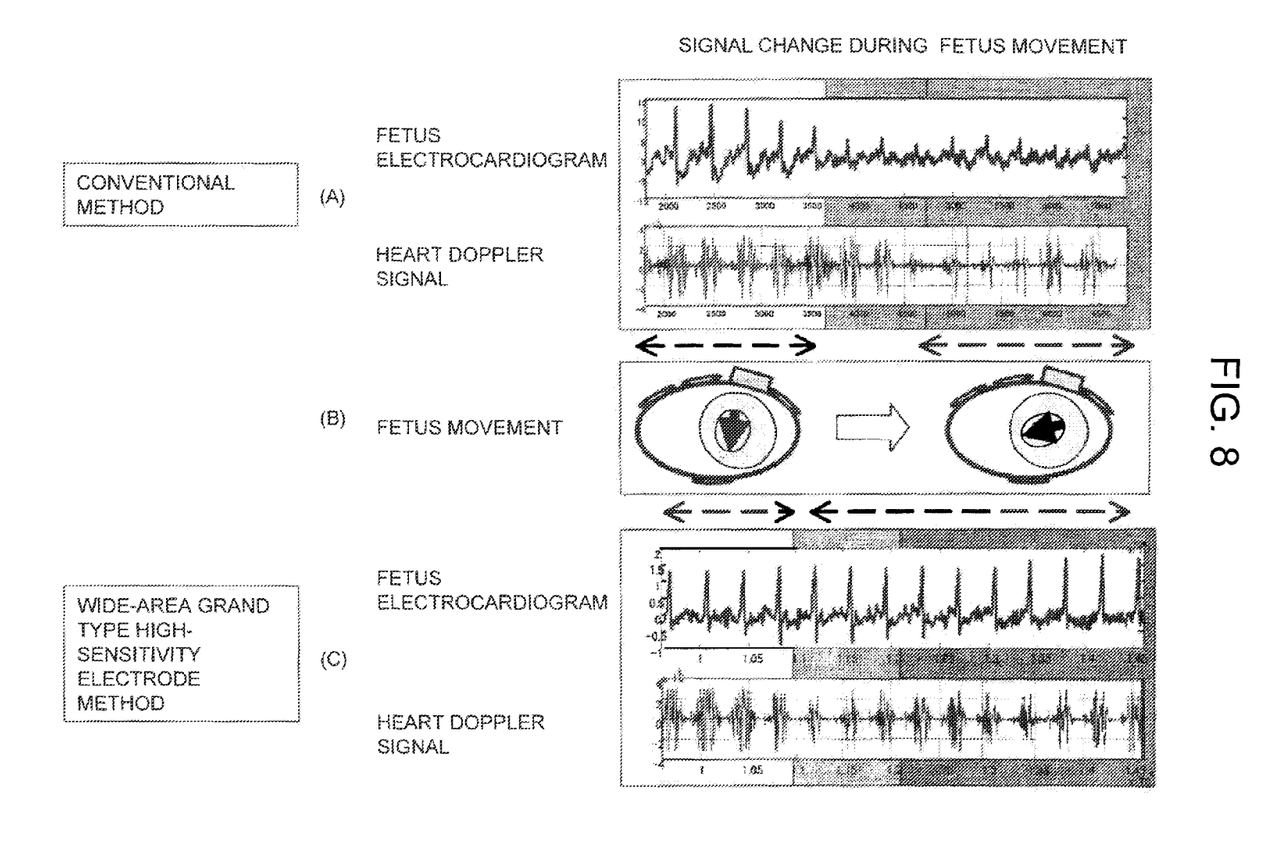
FIG. 8 shows diagrams illustrating measurement examples of the fetus electrocardiogram and fetus heart Doppler signals according to the present invention during fetus movements at 38 weeks of gestation.

FIG. 8 shows diagrams illustrating measurement examples of the fetus electrocardiogram and a fetus heart Doppler signals during fetus movements at 38 weeks of gestation. In FIG. 8, FIG. 8(A) illustrates a fetus electrocardiogram and fetus heart Doppler signals by the conventional method, FIG. 8(B) illustrates a schematic diagram of fetus movements, and FIG. 8(C) illustrates a fetus electrocardiogram and fetus heart Doppler signals by the wide-area ground type high-sensitivity electrode method according to the present invention.

From these figures, it can be seen that, in the conventional method, potentials of R-waves in the fetus electrocardiogram has attenuated due to fetus movements to thereby make impossible the measurement of the fetus electrocardiogram (FIG. 8(A)). In contrast, in the method according to the present invention (FIG. 8C), fetus electrocardiogram signals have been stably measured even during fetus movements.

The present invention, which uses the region-variable ground electrode for electrode optimization, is unprecedented to date. The present invention realizes a wide-area and high-sensitivity measurement, and is of great importance in the measuring technique for bioelectrical signals on the order of microvolts.

Therefore, useful application examples of the present invention, other than the measurement of fetus electrocardiogram signals described in the embodiments, include measurements of bioelectrical signals on the order of microvolts, such as adult or neonatal brain waves, electromyogram, nerve fascicle potential, and adult His-bundle potential. Moreover, fetus electrocardiograms for animals such as horses, cows, sheep, rabbits, mice, etc. can be also measured.

According to the present invention, the wide-area ground type high-sensitivity electrode, which combines the high input impedance electrodes, the region-variable ground electrodes and the differential amplifier, and the optimization of this wide-area ground type high-sensitivity electrode, allow a convenient and extensively applicable measurement of fetus electrocardiogram signals capable of measuring fetus electrocardiogram signals even during the fetus movements and even at a gestational age during which the measured potential is low, without the need for reattaching the electrodes and providing any special space such as a shield room, even if the mother is either a hospitalized or ambulant pregnant woman.

INDUSTRIAL APPLICABILITY

According to the bioelectric potential measuring device including the fetus electrocardiogram by wide-area ground type high-sensitivity electrode method according to the present invention can be applied not only to a measuring device such as a fetus monitor (fetus electrocardiograph) playing a core role in obstetric medical services, but also to various obstetric fields including fetus diagnosis in the form of an automated optimal measuring device used during fetus movements or signal degradation.

Furthermore, the bioelectric potential measuring device produced by the present invention can be extensively used for brain wave measurement, electromyographic measurement, nerve fascicle potential measurement, and animal fetus electrocardiogram measurement.

The invention claimed is:

1. A fetus electrocardiogram signal measuring method for measuring, in an on-line manner, fetus electrocardiogram waveforms from a plurality of electrodes for attachment to a breast and an abdomen of a mother's body during pregnancy, the method comprising the steps of:
   (a) providing a high input impedance electrode section having an impedance of 100 GΩ or above for directly acquiring biological information, the high input impedance electrode section comprising:
      a skin contact electrode section composed of a plurality of measurement electrodes and a reference electrode, each electrode being a high input impedance electrode of an impedance of 100 GΩ or above;
      a preamplification section having a characteristic of a high input impedance of 100 GΩ or above; and
      a shield cable,
   (b) providing a region-variable ground electrode section for addressing various positional variations of the fetus, the region-variable ground electrode section being constituted of one or more region-variable ground electrodes;
   (c) providing a differential amplification section serving as a main measuring member and having a differential characteristic; and
   (d) providing an electrode optimization computing section that selects an optimal ground electrode region and an optimal electrode out of combinations of all of the electrodes, in order to optimally control the fetus position/state so that a maximum signal with low noise can be measured,
   wherein the preamplification section is a preamplifier including an operational amplifier located between the differential amplification section and an electrode measurement point; and
   wherein the preamplification section reduces a bias current flowing from the region-variable ground electrode section to the differential amplification section down to a current on an order of picoamperes, and performs a potential difference measurement with a high sensitivity better than ±1 μV.

2. The fetus electrocardiogram signal measuring method according to claim 1, wherein each of the plurality of measurement electrodes and reference electrode is provided with a dielectric metal, an electrically-conductive polymeric gel, and connecting means therebetween.

3. The fetus electrocardiogram signal measuring method according to claim 1,
   wherein the region-variable ground electrode section is a variable ground electrode capable of changing a measurement region of a biological signal in response to a change in a fetus position or in a fetus size depending on a gestational age, and to fetus movements; and
   wherein the region-variable ground electrode section comprises:
      region-variable ground electrodes each constituted of one or more plane electrodes; and
      an electrode optimal region constituting section constituting an optimal region on a basis of optimal region information output from the electrode optimization computing section.

4. The fetus electrocardiogram signal measuring method according to claim 3,
   wherein the region-variable ground electrodes are constituted of basic sheet ground electrodes each having one or more basic unit electrodes insulated from each other; and
   wherein the basic sheet ground electrode can be freely changed in size/shape.

5. The fetus electrocardiogram signal measuring method according to claim 3,
   wherein the electrode optimal region constituting section comprises:
      a threshold circuit that selects a combination of ground electrodes including fetus electrocardiogram components of a definite amount or above, out of the optimal region information input from the electrode optimization computing section; and
      a relay circuit that implements the information obtained from the threshold circuit by a switch connection; and
   wherein, on a basis of the optimal region information output from the electrode optimization computing section, a size/shape of each of the ground electrodes is changed by freely combining a plurality of the basic sheet ground electrodes for attachment to a biological body and connecting them to each other by the relay circuit, to thereby realize optimal ground electrodes matched with fetus movements/fetus positional variations.

6. The fetus electrocardiogram signal measuring method according to claim 1,
   wherein the differential amplification section comprises:
      the high input impedance electrode section;

a differential amplifier for amplifying and differentiating a signal from the input of the region-variable ground electrode;
a multiplexer that converts multiple inputs into a single input; and
an A/D converter;
wherein a potential of each measurement channel output from a signal output section is obtained by subtracting a difference between the potential of the reference electrode and a ground potential from a difference between the potential of each channel and the ground potential; and
wherein, by placing the reference electrode and the region-variable ground electrode at the same region, the voltage difference between in-phase voltage signals of the reference electrode and region-variable ground electrode is made to be zero, and the potential of each measurement channel is made to be the difference between the potential of each channel and the potential of the variable region ground electrode.

7. The fetus electrocardiogram signal measuring method according to claim 1, wherein the electrode optimization computing section comprises:
a fetus electrocardiogram signal recognition section that recognizes a fetus electrocardiogram signal;
a ground electrode recognition section that, on a basis of each channel information from the fetus electrocardiogram signal recognition section, recognizes a basic unit ground electrode (indifferent ground electrode) including no fetus electrocardiogram signal in every measurement channel, and a variable ground electrode (optimal variable ground electrode) including fetus electrocardiogram signals to a maximum degree in any measurement channel;
a measurement electrode recognition section that recognizes a measurement electrode (indifferent measurement electrode) by which no fetus electrocardiogram signal is measured when the optimal variable ground electrode is used; and
a basic computing section capable of cancelling noise that is electrode noise other than ground electrode-derived noise and that is common to all the measurement electrodes, by taking the difference in potential between each of the measuring electrodes and the indifferent electrode.

8. A fetus electrocardiogram signal measuring device for measuring, in an on-line manner, fetus electrocardiogram waveforms from a plurality of electrodes for attachment to a breast and an abdomen of a mother's body during pregnancy, the device comprising:
a high input impedance electrode section having an impedance of 100 GΩ or above for directly acquiring biological information, the high input impedance electrode section comprising:
a skin contact electrode section composed of a plurality of measurement electrodes and a reference electrode, each electrode being a high input impedance electrode of an impedance of 100 GΩ or above;
a preamplification section having a characteristic of a high input impedance of 100 GΩ or above; and
a shield cable,
a region-variable ground electrode section for addressing various positional variations of the fetus, the region-variable ground electrode section being constituted of one or more region-variable ground electrodes;
a differential amplification section serving as a main measuring member and having a differential characteristic; and
an electrode optimization computing section that selects an optimal ground electrode region and an optimal electrode out of a combination of all of the electrodes, in order to optimally control the fetus position/state so that a maximum signal with low noise can be measured,
wherein the preamplification section is a preamplifier including an operational amplifier located between the differential amplification section and an electrode measurement point; and
wherein the preamplification section is configured to:
reducing a bias current flowing from the region-variable ground electrode section to the differential amplification section down to a current on an order of picoamperes, and
performing a potential difference measurement with a high sensitivity better than ±1 μV.

9. The fetus electrocardiogram signal measuring device according to claim 8, wherein each of the plurality of measurement electrodes and reference electrode is provided with a dielectric metal, an electrically-conductive polymeric gel, and connecting means therebetween.

10. The fetus electrocardiogram signal measuring device according to claim 8;
wherein the region-variable ground electrode section is a variable ground electrode capable of changing a measurement region of a biological signal in response to a change in a fetus position or in a fetus size depending on a gestational age, and to fetus movements; and
wherein the region-variable ground electrode section comprises:
region-variable ground electrodes each constituted of one or more plane electrodes; and
an electrode optimal region constituting section constituting an optimal region on a basis of optimal region information output from the electrode optimization computing section.

11. The fetus electrocardiogram signal measuring device according to claim 10,
wherein the region-variable ground electrodes are constituted of basic sheet ground electrodes each having a width of one or more basic unit electrodes insulated from each other; and
wherein the basic sheet ground electrode can be freely changed in size/shape.

12. The fetus electrocardiogram signal measuring device according to claim 10,
wherein the electrode optimal region constituting section comprises:
a threshold circuit that selects a combination of ground electrodes including fetus electrocardiogram components of a definite amount or above, out of the optimal region information input from the electrode optimization computing section; and
a relay circuit that implements the information obtained from the threshold circuit by a switch connection; and
wherein, on a basis of the optimal region information output from the electrode optimization computing section, a size/shape of each of the ground electrodes is changed by freely combining a plurality of the basic sheet ground electrodes for attachment to a biological body and connecting them to each other by the relay circuit, to thereby realize optimal ground electrodes matched with fetus movements/fetus positional variations.

13. The fetus electrocardiogram signal measuring device according to claim 8,
wherein the differential amplification section comprises:
the high input impedance electrode section;
a differential amplifier for amplifying and differentiating a signal from the input of the region-variable ground electrode;
a multiplexer that converts multiple inputs into a single input; and
an A/D converter;
wherein a potential of each measurement channel output from a signal output section is obtained by subtracting a difference between the potential of the reference electrode and a ground potential from a difference between the potential of each channel and the ground potential; and
wherein, by placing the reference electrode and the region-variable ground electrode at the same region, the voltage difference between in-phase voltage signals of the reference electrode and region-variable ground electrode is made to be zero, and the potential of each measurement channel is made to be the difference between the potential of each channel and the potential of the region-variable ground electrode.

14. The fetus electrocardiogram signal measuring device according to claim 8, wherein the electrode optimization computing section comprises:
a fetus electrocardiogram signal recognition section that recognizes a fetus electrocardiogram signal;
a ground electrode recognition section that, on a basis of each channel information from the fetus electrocardiogram signal recognition section, recognizes a basic unit ground electrode (indifferent ground electrode) including no fetus electrocardiogram signal in every measurement channel, and a variable ground electrode (optimal variable ground electrode) including fetus electrocardiogram signals to a maximum degree in any measurement channel;
a measurement electrode recognition section that recognizes a measurement electrode (indifferent measurement electrode) by which no fetus electrocardiogram signal is measured when the optimal variable ground electrode is used; and
a basic computing section capable of cancelling noise that is electrode noise other than ground electrode-derived noise and that is common to all the measurement electrodes, by taking the difference in potentials between each of the measuring electrodes and the indifferent electrode.

* * * * *